United States Patent [19]
Wilson et al.

[11] Patent Number: 6,142,309
[45] Date of Patent: Nov. 7, 2000

[54] METHOD OF DETERMINING THE AMOUNT OF RESIDUE IN CARBON BLACK

[75] Inventors: James R. Wilson, Melrose, Mass.; Achille Bucci, Russi Ra; Maurizio Lucchi, Modena, both of Italy; Angela G. Kimball, Harvard, Mass.

[73] Assignee: Cabot Corporation, Boston, Mass.

[21] Appl. No.: 09/185,718

[22] Filed: Nov. 4, 1998

[51] Int. Cl.[7] ................................................. B03B 7/00
[52] U.S. Cl. .............................. 209/12.1; 209/3; 209/5; 209/38; 209/234; 209/237
[58] Field of Search ................................ 209/3, 4, 5, 7, 209/12.1, 38, 645, 234, 592, 237

[56] References Cited

U.S. PATENT DOCUMENTS

| | | | |
|---|---|---|---|
| 2,612,262 | 9/1952 | Symington et al. | 209/5 |
| 3,536,264 | 10/1970 | Helton et al. | 241/4 |
| 3,615,297 | 10/1971 | Dille et al. | 48/196 R |
| 3,826,365 | 7/1974 | Mercade | 209/5 |
| 4,259,181 | 3/1981 | Leon et al. | 209/231 |
| 4,303,204 | 12/1981 | Weston | 241/16 |
| 4,482,460 | 11/1984 | Kandler et al. | 210/706 |
| 4,530,769 | 7/1985 | Wolter et al. | 210/769 |
| 4,693,879 | 9/1987 | Yoshimura et al. | 423/461 |
| 4,871,248 | 10/1989 | Hoffman | 356/36 |
| 5,112,782 | 5/1992 | Brown et al. | 501/144 |
| 5,522,924 | 6/1996 | Smith et al. | 106/488 |
| 5,843,315 | 12/1998 | Baughn et al. | 210/723 |
| 5,974,167 | 10/1999 | Reszier | 382/141 |

FOREIGN PATENT DOCUMENTS

58017172  1/1983  Japan ................................. C09C 1/48

OTHER PUBLICATIONS

Encyclopedia of Chemical Processing and Design, John J. McKetta, 1978, vol. 6, pp. 236–240, 243.

ASTM for Carbon Black—Sieve Residue, Designation: D 1514–90 pp. 293–295.

*Primary Examiner*—Donald P. Walsh
*Assistant Examiner*—David A Jones

[57] ABSTRACT

Test methods are provided for determining the amount of contaminants in a carbon black sample. The test procedures include screening a known amount of carbon black to separate larger particles in the sample from smaller particles. The sample and/or separated larger particles are treated with a separating force to disperse larger agglomerates of carbon black into smaller aggregates of carbon black and to separate contaminants from carbon black aggregates. The treated sample or separated larger particles can then be screened to again separate larger particles from smaller particles. The separating force may be a water wash stream which contacts the sample or separated larger particles at a pressure of from about 15 psi to about 35 psi. The separating force may instead or additionally be generated by a dispersing agent which can be combined with the sample or separated larger particles in an amount or concentration sufficient to disperse larger agglomerates of carbon black into smaller carbon black aggregates. The measured weight of the separated contaminants and the measured weight of the carbon black sample can be used to determine the weight percent of certain contaminants in the carbon black sample.

44 Claims, 1 Drawing Sheet

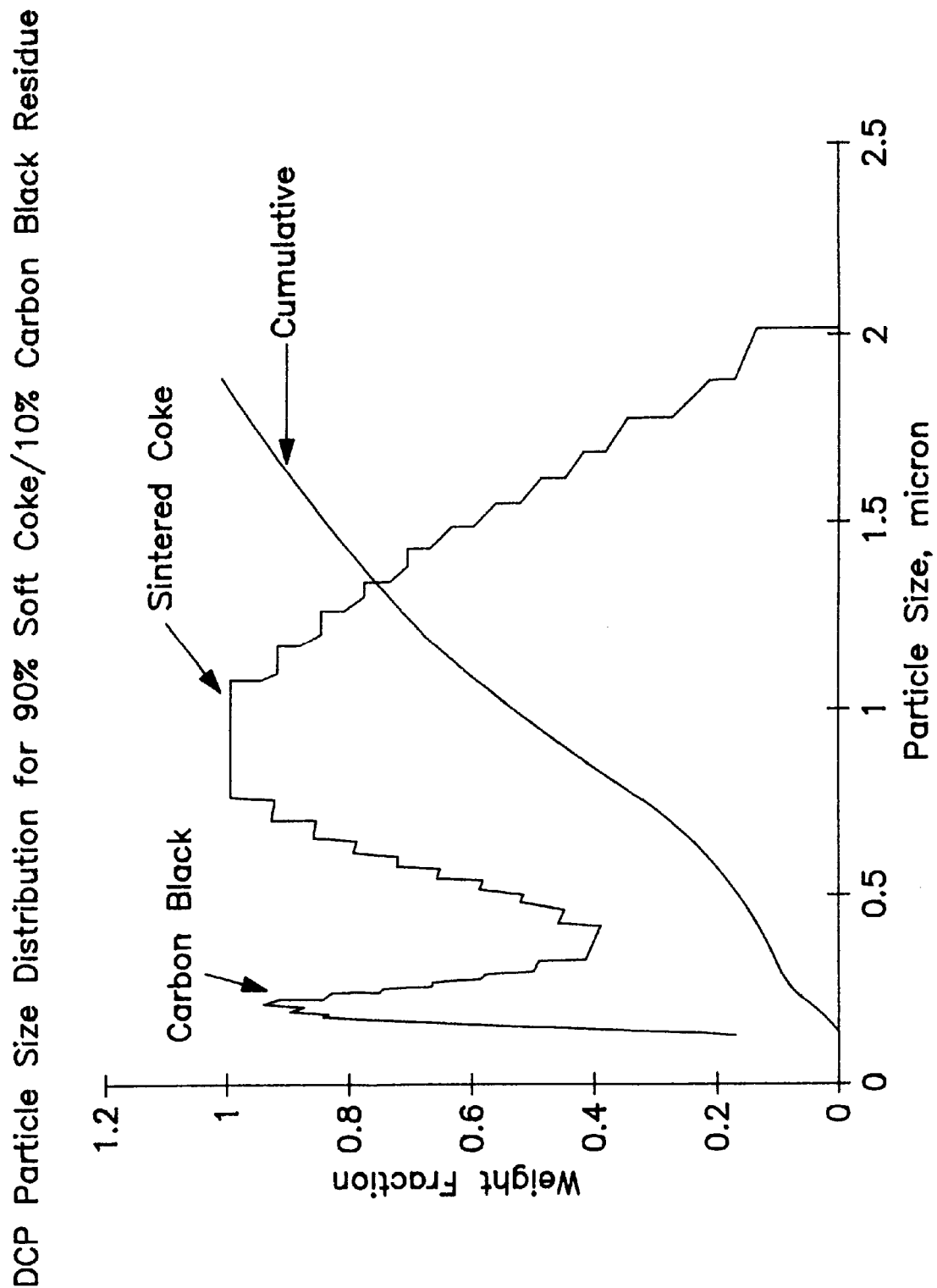

METHOD OF DETERMINING THE AMOUNT OF RESIDUE IN CARBON BLACK

FIELD OF THE INVENTION

The present invention relates to a method of determining the amount of residue in a carbon black sample. The present invention also relates to a method of predicting macro defects in an extruded composition filled with the carbon black.

BACKGROUND OF THE INVENTION

Carbon blacks are widely used as reinforcing agents for elastomeric compositions. Carbon blacks contain residues or contaminants including soft coke, magnetic particles, and large agglomerates of carbon black that cannot be broken down. Carbon blacks having relatively high amounts of contaminants or relatively large contaminant particles tend to cause macro defects when used in extruded compositions, for example, an extruded elastomeric and/or polymeric composition such as a rubber sealant, a door seal, a car gasket, or other profile extrudates. There is a need to determine the amount of contaminants in a carbon black so that the suitability of the carbon black for use as a filler in an extruded composition can be accurately predicted.

A test method for determining the amount of residue in a carbon black sample is ASTM test method D-1514. Unfortunately, ASTM D-1514 does not accurately take into account the amount of soft coke in the sample as residue. Thus, ASTM D-1514 cannot be relied upon to accurately provide a prediction of macro defect formation in an extrudable composition containing carbon black. Results of the ASTM D-1514 test method have proven not to correlate with an extruded tape test wherein a thin test tape of a compounded material is extruded and visually inspected for macro defects. The number of macro defects is counted either visually or using an image analyzer. This method of counting defects above 200 $\mu$m in diameter on the surface of an extruded tape has been shown to accurately predict product performance in extruded filled ethylene-propylene diene rubber (EPDM) compositions.

Accordingly, there is a need to develop a method of determining the amount of contaminants, including soft coke, in a carbon black sample. It is desirable to develop a carbon black residue test that correlates well with the extruded tape test and which can accurately predict product performance of extruded products containing carbon black.

SUMMARY OF THE INVENTION

The present invention relates to a method of determining the amount of sieve residue present in a carbon black sample. The test is designed to detect contaminants which may lead to surface defects in extrusion profiles. The test results from the present invention correlate with the number of defects greater than 200 microns in the extruded tape test. The contaminants detected according to the present test methods include soft coke which is normally lost during the rub-out step of the ASTM D-1514 test method. Soft coke is a source for surface defects in extrusion products, particularly in soft polymers, such as EPDM. Soft coke is generally defined as a friable carbonaceous residue produced during the manufacture of carbon black, for example, in the furnace manufacture of carbon black.

Undesirably large clusters of carbon black aggregates, herein referred to as carbon black agglomerates, may also be considered contaminants. Carbon black agglomerates are considered contaminants for purposes of the present invention when (1) they cannot pass through a 120 mesh screen after being washed with a 25 psi stream of water, and (2) they can not pass through a 120 mesh screen after being treated with a dispersing agent that includes an aqueous solution of at least one organic solvent, for example, an aqueous solution of 2-butoxy ethanol and monoethanolamine. Carbon black agglomerate contaminants can also be separated and detected from a carbon black sample to be tested according to the present invention.

The present invention particularly relates to a method of determining the amount of contaminants in a carbon black sample, wherein a known amount of carbon black is screened to separate larger particles in the sample from smaller particles. The separated larger particles are then contacted with a dispersing agent comprising at least one organic component in an amount effective to disperse larger agglomerates of carbon black into smaller aggregates of carbon black. The dispersing agent preferred is effective to disperse agglomerated particles of carbon black that do not pass through a 120 mesh screen into smaller carbon black aggregates that do pass through a 120 mesh screen. Carbon black agglomerates that do not disperse into carbon black aggregates which pass through a 120 mesh screen, are considered carbon black contaminants. The dispersing agent preferably also separates non-carbon black contaminants from the carbon black aggregate and agglomerate particles in the sample.

After contact with the dispersing agent, the resulting dispersion is then screened to separate larger particle contaminants which do not pass through the screen from smaller particles in the dispersion which do not pass through the screen. The weight of the separated larger particle contaminants can then be measured and the contaminants can be further treated and analyzed.

According to the present invention, a method is provided for determining the amount of contaminants in a carbon black sample, wherein a known amount of carbon black is screened to separate larger particles in the sample from smaller particles, a magnetic force is applied to the separated larger particles to separate magnetic contaminants in the larger separated particles from non-magnetic components of the larger separated particles, and the amount of separated magnetic contaminants is measured.

Methods of determining the total amounts and relative amounts of various types of contaminant residues are also provided wherein a carbon black sample is treated with both a dispersing agent according to the present invention and a magnetic force.

BRIEF DESCRIPTION OF THE DRAWINGS

The present invention may be more fully understood with reference to the attached drawing, wherein the FIGURE is a disc centrifuge photosedimentometer graph showing the particle size distribution of a contaminant residue containing 90% by weight soft coke and 10% by weight carbon black agglomerates.

It is to be understood that both the foregoing general description and the following detailed description are exemplary and explanatory only and are intended to provide further explanation of the present invention, as claimed.

DETAILED DESCRIPTION OF THE INVENTION

Methods of determining the amount of contaminant residues in a carbon black sample are provided by the present invention. According to a method of the present invention, a known amount of carbon black is screened to separate larger particles in the sample from smaller particles. For example, a 120 mesh screen can be used according to the present invention to separate contaminants, which do not pass through the screen, from non-contaminants, which do pass through the screen. For purposes of macro defect prediction for an extrudable composition, contaminants can preferably be considered as those particles which do not pass through a 120 mesh screen. Accordingly, contaminants can be considered those having an average particle size diameter that are larger than about 125 $\mu$m.

According to the present invention, the separated larger particles which do not pass through the screen are then combined with a dispersing agent comprising at least one, and preferably two, organic components. The dispersing agent may be present, for example, in an aqueous solution, in a concentration or amount effective to disperse larger agglomerates of carbon black from the separated larger particles into smaller aggregates of carbon black. The dispersing agent also preferably separates contaminants in the sample from carbon black aggregates and agglomerate particles in the separated residue. The resulting dispersion is then screened to separate larger particle contaminants from smaller particles in the dispersion. The weight of the collected treated residue can then be measured and the part per million (ppm) of separated larger particle contaminants can be determined from the measured weights.

According to another aspect of the present invention, a method is provided for determining the amount of contaminants in a carbon black sample wherein a known amount of carbon black is screened to separate larger particles in the sample from smaller particles and a magnetic force is applied to the separated larger particles to separate magnetic contaminants from non-magnetic components. The amount of separated magnetic contaminants can be measured and used to calculate the ppm of magnetic contaminants in the sample.

Methods of determining the total amounts and relative amounts of various types of contaminant residues are also provided wherein a carbon black sample is treated with both a dispersing agent according to the present invention and a magnetic force.

According to the present invention, the dispersing agent includes an aqueous solution, dispersion, emulsion, suspension or mixture of at least one organic solvent. The dispersing agent may include a glycol ether, for example, 2-butoxyethanol. The dispersing agent may instead, or additionally include an alcohol amine, for example, monoethanolamine. The dispersing agent may also include an alcohol alkoxylate, for example, nonyl phenyl ethoxylate.

Preferably, the dispersing agent includes two or more compounds selected from a glycol ether, an alcoholamine, and an alcohol alkoxylate. More preferably, the dispersing agent includes a glycol ether, an alcoholamine, and an alcohol alkoxylate. The dispersing agent can preferably be an aqueous solution containing from about 0.1% by weight to about 15% by weight, more preferably from about 1.0% by weight to about 10% by weight of a glycol ether. More preferably, the dispersing agent is an aqueous solution containing from about 5% by weight to about 7% by weight of a glycol ether. The dispersing agent can preferably be an aqueous solution containing from about 0.1% by weight to about 10% by weight, more preferably from about 0.5% by weight to about 5% by weight of an alcohol amine. More preferably, the dispersing agent is an aqueous solution containing from about 1% by weight to about 3% by weight of an alcohol amine. The dispersing agent can preferably be an aqueous solution containing from about 0.1% by weight to about 5% by weight, more preferably from about 0.5% by weight to about 3% by weight of an alcohol alkoxylate. More preferably, the dispersing agent is an aqueous solution containing from about 1% by weight to about 1.5% by weight glycol ether.

According to the present invention, the dispersing agent is preferably an aqueous solution including both 2-butoxyethanol and ethanolamine, and optionally also includes nonyl phenol ethoxylate. More preferably, the dispersing agent can be an aqueous solution containing from about 5% by weight to about 7% by weight 2-butoxyethanol, from about 1% by weight to about 3% by weight ethanolamine, and from about 1% by weight to about 1.5% by weight nonyl phenol ethoxylate.

If the separated larger particles from the initial screening step are mixed with an amount of a dispersing agent solution, the amount of solution to mix the particles with is preferably at least about 10 times the weight of the particles to be treated, more preferably, at least about 100 times the weight of the separated larger particles to be treated. For example, if a 2000 g sample of carbon black provides 0.5 g of particles greater than 120 mesh size, the 0.5 g of particles is preferably treated with about 50 ml of an aqueous solution of the dispersing agent.

The separating methods of the present invention, and the results from those methods, can be used to determined the concentration of different residue components in the sample. The test results achieved according to the present invention can be compared to predetermined values which fall on either side of and approximate to an acceptable macro defect formation limitation. Such a comparison can be used to accurately predict the amount of macro defect formation that would occur if the carbon black sample is used as a filler in an extrudable composition. A comparison of the result achieved to known standards for a carbon black used at a particular loading in a known extrudable elastomeric and/or polymeric component can provide an accurate prediction of the amount of macro defect formation that would occur if the sampled carbon black were used in the same composition having the particular elastomeric and/or polymeric component and the particular loading of carbon black in the composition. For example, the determined concentration could be compared to predetermined values achieved by using standards derived from testing carbon blacks of known residue amounts and known acceptability or rejectability based on tested macro defect formation of an extruded product, such as an extruded EPDM composition.

Equipment which can be used for carrying out the methods of the present invention can include stainless steel sieves, for example, U.S. Standard Sieves preferably having mesh sizes of 60 and 120 mesh although other mesh sizes can be used. Preferably, a filtering apparatus is used to hold the sieves, for example, the drawing filters 4-C-900, 4-C-901, 4-C-902, from Cabot Corporation, Boston, Mass. Sieve and filtering apparatus are available from Titan Specialties, Inc. P.O. Box 2315, Pampa, Tex. 70066-2316. In place of a drawing filter, a cartridge filter of 40 micron ($\mu$m) or smaller mesh size can be used. Analytical balances with respective sensitivities of 0.1 mg, and 0.1 g can be used to weigh the resulting residues. Preferably, weighing dishes are used to measure the weight of the residues with a balance having a 0.1 mg sensitivity. An oven capable of maintaining a temperature of about 125+/−1° C. can be used to dry separated residue. A horseshoe magnet, for example, an ALMICO three pound (1361 g) pull magnet available from Sargent-Welch, Skokie, Ill. 60076 (catalog #S44380B) can be used. A 50 ml glass beaker is preferably used to treat collected residue with a dispersing agent of the present invention. A magnetic stirring bar and a stirrer or stir rod can be used to magnetically separate magnetic contaminants in the collected residue from non-magnetic contaminants.

A composite sample of carbon black to be tested is preferred over a spot sample because spot samples can give misleading results. Low levels of soft coke are randomly distributed in carbon black and an accurate measurement of soft coke requires good sampling procedures. The smaller portions which constitute the composite sample should be taken from the bottom of a feed station for a conveying screw chest, at least one meter (m) from the input or outlet of the chest. It is preferred to collect sample portions from a location as close as possible, but not within one meter of, the feed station silo inlet.

Preferably, the composite, incremental sample should represent a minimum 8 hours of production with at least about 150 g of product collected every 15 minutes. The sample should be homogenized prior to testing, using an adequately sized riffle-splitter, for example, as per the ASTM D-5817 test method. Riffle splitters which can be used include those available from Glen Mills, Inc., Clifton, N.J., Quantachrome, Boynton Beach, Fla., and Gilson Company, Inc., Worthington, Ohio. Stored samples should be homogenized each time prior to re-sampling and testing.

The composite sample is preferably washed with water supplied through a pressure-controlled nozzle. To prepare for the water washing, water pressure flowing through should be regulated with a valve to be within the range of from about 15 psi to about 35 psi, preferably from about 22 psi to about 27 psi, for example, about 25+/−1 psi. Higher water pressures can be used but tend to break up soft coke contaminants to a size small enough to fit through the sieve, and thus the pulverized or broken soft coke may be undetected. Lower water pressures require longer wash times and fail to adequately break carbon black agglomerates into aggregates of a more desirable size. Carbon black agglomerates that are broken down to aggregates smaller than a 120 mesh size particle are not considered contaminants as such agglomerates are typically broken small enough to not cause visible macro-defects in extruded polymeric compositions containing the carbon black.

The flow rate of water coming out of the nozzle should be regulated to be about 1.5 gal/min. Then, a clean 2" diameter, 120 mesh ASTM approved sieve having a stainless steel screen is attached to the bottom of a funnel holder and water is allowed to flow through the screen for about two to about five minutes. The water nozzle should be kept about ¾ of an inch above the screen. Other distances can be used, but ¾ of an inch is preferred. The water flow is then stopped and the screen is examined for particles. If no particles are observed, the apparatus is ready for water washing a carbon black composite sample. A baffled six inch extension muffler can be placed after the screens to reduce noise.

Other mesh sizes can be used, for example, a 325 mesh sieve or a 625 mesh sieve. Longer wash times are necessary when tighter mesh sieves such as a 325 mesh sieve is used, but a more accurate determination of residue amount can be achieved.

The sample of carbon black to be analyzed preferably weighs at least about 1000 g, for example, from about 1000 g to about 3000 g, and more preferably from about 1500 g to about 2500 g, for example, about 2000 g, and is weighed to the nearest 0.1 g. If a 2000 g sample is not available, as much carbon black as possible should be used and the weight of the sample recorded.

Water flow through the nozzle is then started by opening the valve to the nozzle. The sample of carbon black is then added slowly to the funnel to prevent plugging of the screen. A gentle stream of water from the hose can be used to wash down any carbon black on the sides of the funnel. Washing should continue until the wash water coming through the screen is clear. After the entire sample of carbon black has been washed, the screen is removed from the bottom of the funnel to ensure that all residue on the screen is retained on the screen.

The resulting residue can then be chemically and/or magnetically treated to further separate non-carbon black large particles from carbon black agglomerates, carbon black aggregates, and from non-carbon black small particles. For example, a squirt bottle containing a dispersing agent like SPEEDBALL™ cleaner available from The Butcher Company, Marlborough, Ma., can be used to rinse the residue from the 120 mesh screen into a 50 ml glass beaker. An additional dispersing agent or an additional amount of the same dispersing agent, for example, SPEEDBALL™ cleaner, is then added to the beaker as needed to bring the volume of the mixture in the beaker to approximately 40 ml.

A 1.0" magnetic stir bar can be placed into the solution and stirred for 15 minutes to magnetically treat the mixture. The stir bar is then removed from the beaker using a stir bar retriever. Both the stir bar and retriever are then rinsed with de-ionized water into a second beaker. No metallic particles should remain on either the stir bar or on the retriever.

The remaining dispersing agent solution/mixture in the 50 ml beaker is preferably then poured through a stack of progressively higher mesh sieves, for example, through a 60 mesh sieve then through a 120 mesh sieve which are set in a large beaker, for example, a 3000 ml plastic beaker. The contaminants remaining on the sieves constitute the total non-magnetic grit residue.

Once the dispersing agent solution/mixture is collected in the 3000 ml beaker, the sieves are then removed from the beaker continually rinsed with de-ionized water. When SPEEDBALL™ or other similar types of dispersing agents are used, the waste should be handled and disposed of as hazardous waste.

The screens containing the remaining residue are then dried in any manner, such as under an infrared heat lamp or natural convection oven. It is preferable not to stack the screens when drying. When the screens appear dry, usually within from about 10 minutes to about 15 minutes, they are removed, e.g., from the heat lamp or oven and allowed to cool. Cooling should take about ten minutes.

To collect the residue, a clean stiff bristle brush is used to gently brush the residue from the sieve(s) into a clean tared aluminum weighing dish. The dish is then weighed and the weight of the collected, dried residue is measured to the nearest 0.1 mg.

The weight (ppm) of the residue from each screen can be calculated using the following equation:

$$R(ppm) = \frac{W \times 10^6}{SW}$$

wherein R is the ppm sieve residue of the washed and treated sample, W is the weight in grams of the sieve residue, and SW is the weight of sample, preferably about 2,000 g.

The weight of the residue can be determined in ppm units for both the 60 mesh sieve and the 120 mesh sieve. The total residue from the sum of both screens can be reported as the total 120 mesh sieve particle size, or greater, residue.

According to the present invention, fluffy black can also be tested, though it may present some difficulties in both cleanliness and speed of washing. When fluffy black is analyzed, a cover is preferably used over the funnel and an additional rinse hose is used to reduce dust emissions.

Any other type of carbon black can be tested according to the present invention, with the exception of oil-treated carbon blacks.

The apparatus should be kept clean at all times to prevent contamination. The sieves should be examined each time they are used to make sure no cracks or holes have developed. Sieves should be removed from the holder daily for cleaning and storing purposes.

Screens can be reused, but must be thoroughly cleaned before reuse. Two preferred methods of cleaning the screens include sonifying the screen in a dispersing agent, such as SPEEDBALL™ cleaner, for at least about 10 minutes, and cleaning the sieve by back purging water through the sieve for at least about two minutes.

As a check on the thoroughness of removing the non-dispersible agglomerated carbon black, tests can preferably be performed on the residue. An image analysis of the separated larger particle contaminants can be used to determine the particle size distribution and the number of particles per unit weight of the separated larger particle contaminants. One test is a scanning electron microscopy (SEM) examination of the residue. Soft coke particles appear similar to those of agglomerated carbon black in a scanning electron micrograph, except that the fused spherical soft coke particles are typically 5 to 10 times larger than carbon black particles, which is apparent from the SEM examination. The percentage of soft coke and agglomerated black can be estimated from an SEM micrograph by counting the number of each type of particle in a given number of residue particles. Another test for soft coke is the standard Cabot Disc Centrifuge Photosedimentometer (DCP) wherein a scan is taken of the SPEEDBALL™ treated water washed residue. A DCP scan can show a bimodal distribution with an ascertainable percentage of the integrated area being due to the larger soft coke residue. The ascertainable percentage is indicative of the percentage of soft coke residue in the total residue.

Other mesh screens can be used to separate the residues. More contaminants can be separated from a sample if a smaller particle size sieve is used, for example, a 325 mesh sieve. The use of a 325 mesh sieve may be used as a secondary step to further confirm metallic grit content, magnetic residue, and other non-carbon contaminant residue, however, it takes considerably longer to screen a carbon black sample through a 325 mesh sieve than through a 120 mesh sieve. It takes about 60 minutes to screen 2000 g of carbon black through a 325 mesh screen.

Additional steps can be used to determine more than just the total residue information. The amount of soft residue can be distinguished from the amount of hard residue. For example, the washed and treated total residue may be rubbed-out with a finger tip on smooth, hard paper using finger light pressure to remove carbon black. When the white paper no longer shows any smears, the remaining residue is preferably brushed onto a tared weighing dish and weighed to the nearest 0.1 mg, using an analytical balance. The difference between this value and the total residue is the total amount of soft coke.

The residue remaining after rubbing-out and determining the amount of soft coke may be transferred onto a paper filter and all the magnetic particles can be removed using a magnet. The remaining non-magnetic residue can then be brushed onto a tared weighing dish and weighed to nearest 0.1 mg using an analytical balance. The difference between this value and the residue weight after rubbing out the soft coke is the magnetic residue.

The remaining non-magnetic residue can then be placed into a crucible previously treated for one hour at 850° C. The crucible with the non-magnetic residue therein can then be placed in a furnace set at 850° C. for 30 min, or conditions sufficient to transform the stainless steel into a magnetic form and to lose hard coke to combustion. The hot crucible can then be placed in a desiccator and allowed to cool to room temperature. The remaining residue in the crucible is collected and weighed to the nearest 0.1 mg. The difference between this value and the residue after the step described above of removing magnetic residue from the residue on the paper filter, is the hard coke residue.

The residue collected from the crucible is then transferred to another paper filter and the magnetic particles formed from the stainless steel in the crucible are removed using a magnet. The remaining non-magnetic residue can be brushed onto a tared weight dish and weighed to the nearest 0.1 mg. The difference between this value and the hard coke residue value is the amount of stainless steel.

The final remaining non-magnetic residue from the last mentioned step is the inorganic fraction of the residue. The final inorganic residue can be analyzed with appropriate testing equipment, such as a table top x-ray fluorescence analyzer, like a Model 200T XRF analyzer available from Ascoma Instruments Inc. 11675 Jollyville Rd., Austin, Tex. 78759. The Ascoma XRF analyzer is capable of quantifying the level of the remaining elements, such as Al, Si, S, Ca, and Mg. All XRF analyzers are relatively insensitive to $Na^+$. Cations, such as $Na^+$, $K^+$, and $Ca^{++}$ can be analyzed using either atomic absorption spectroscopy or ion chromatography. All anions, such as sulfates and carbonates can also be analyzed using ion chromatography.

The present invention will be further exemplified by reference to the following examples, which are intended to illustrate, not limit, the invention.

EXAMPLES

Preparation of the Sample

A carbon black to be tested had the following specifications:

| | |
|---|---|
| Pellet $I_2$ No. | 27 ± 4 |
| DBPA | 120 ± 4 |
| CDBPA | 80 ± 4 |
| TINT | 44 ± 4 |
| CTAB | 30 ± 4 |
| Spec20 | 80 min |
| 325 Mesh | 100 max |
| 120 Mesh | 30 max |

A composite amount of the carbon black constituting sample portions taken every fifteen minutes over an eight-hour period was collected from the bottom of a feed station conveying screw chest. The location for the collections was about one meter (m) from the silo input of the chest.

At least about 150 g of carbon black sample was collected every 15 minutes. The composite amount was then homogenized and a 2000 g sample was taken from the homogenized composite amount. Homogenization was performed using a Glen Mills Sample Divider having a 50 liter hopper, eight segments, and a 110 Volt, 60 Hz, single phase motor, as per the ASTM D-5817 test method.

Preparation of the Apparatus

First water pressure from the nozzle was regulated to be 25±1 PSI. The flow rate of water coming out of the nozzle was then regulated to be 1.5 gal/min. A clean 2" diameter 120 mesh, ASTM approved stainless steel screen sieve was attached to the bottom of the a funnel as described in the ASTM D-1514 test method. Water was allowed to flow through the screen for three minutes. The water nozzle was kept at ¾ of an inch above the screen. The water flow was then stopped by closing a water supply valve after three minutes of water flow, and the screen was examined for particles. Since no particles were observed on or in the screen, the apparatus was considered ready for use.

Sample Washing

The composite sample was washed with water expelled from a nozzle as described in ASTM test method D-1514, last approved in 1990, and disclosed in the Annual Book of ASTM Standards, Vol. 9.01, 1990, pages 293–295, which Volume is herein incorporated in its entirety by reference.

A 2000 g sample of the homogenized carbon black composite amount was weighed to the nearest 0.1 g and the measured amount recorded. The flow of water was then started by opening the valve to the nozzle. The carbon black sample was slowly added to the funnel to prevent plugging of the sieve screen. A gentle stream of water from the hose was used to wash down any carbon black on the sides of the funnel. The sample and screen were continually washed until the wash water coming through the screen was clear. The screen was then removed from the bottom of the funnel carefully to ensure that all residue was retained on the screen.

Chemical Treatment

A squirt bottle containing SPEEDBALL™ cleaner was used to rinse the residue from the 120 mesh screen into a 50 ml glass beaker. Additional SPEEDBALL™ cleaner was added to the beaker as needed to bring the volume to approximately 40 ml. Next, a 1.0" magnetic stir bar was placed into the solution/mixture in the 50 ml beaker and stirred for 15 minutes. After 15 minutes of stirring, the stir bar was removed from the beaker using a stir bar retriever. Both the stir bar and stir bar retriever were then rinsed with de-ionized water into a second beaker until no metallic particles remained on either the stir bar or the retriever.

The SPEEDBALL™ solution was then poured through a 60 mesh sieve followed by a 120 mesh sieve arranged in a stack. The stack was set in a 3000 ml plastic beaker. The residue collected by both sieves was the total non-magnetic residue. Once the SPEEDBALL™ solution was collected in the 3000 ml beaker, the sieves were removed from the beaker. The SPEEDBALL™ waste that passed through the sieve was collected and disposed of as hazardous waste. The sieves were continually rinsed with de-ionized water.

The rinsed screens containing the non-magnetic residue were then placed under an infrared heat lamp to dry. The sieves were not stacked in the oven. The screens appeared dry in about 10 minutes to about 15 minutes. The screens were then removed from the heat lamp and allowed to cool. Cooling took about 10 minutes.

The resultant residue was then collected by gently brushing the screens with a clean stiff bristle brush onto a clean tared aluminum weighing dish. The dish and its contents were then weighed to the nearest 0.1 mg, and the weight was recorded.

The weight of the residue from each screen was calculated using the following equation:

$$R(ppm) = \frac{W \times 10^6}{SW}$$

wherein R is the weight (ppm) of the sieve residue, W is the weight in grams of the sieve residue, and SW is the weight in grams of the sample washed (2,000 g). The residue was then reported in ppm units for both the 60 mesh sieve and the 120 mesh sieve. Also, the total residue from the sum of both screens was reported as the total 120 and wider mesh residue.

The DCP scan shown in the FIGURE shows a bimodal distribution with over 90% of the integrated area due to the larger soft coke residue and about 10% of the integrated area due to carbon black. Visual inspection of the scan revealed that the residue contained 90% by weight soft coke of particle size greater than 120 mesh and only 10% by weight carbon black stable agglomerates of particle size greater than 120 mesh. Scanning Electron Microscopy could have also or instead been used to determine the amount of soft coke in the residue.

Other embodiments of the present invention will be apparent to those skilled in the art from consideration of the specification and practice of the present invention disclosed herein. It is intended that the specification and examples be considered as exemplary only, with a true scope of the present invention being indicated by the following claims.

What is claimed is:

1. A method of determining the amount of contaminants in a carbon black sample, comprising screening the carbon black sample through a first screen to separate larger particles which do not pass through the first screen from smaller particles that do pass through the first screen, said separated larger particles comprising carbon black agglomerates alone that do not pass through the first screen, soft coke particles that do not pass through the first screen, or both, contacting the separated larger particles with a dispersing agent to form a dispersion, said dispersing agent comprising at least one organic component in an amount effective to disperse at least some of said carbon black agglomerates into smaller aggregates of carbon black that can pass through the first screen, and to separate said soft coke particles from said aggregates of carbon black and said carbon black agglomerates, said dispersion comprising large particle contaminants that do not pass through a second screen and non-contaminant particles that do pass through said second screen, screening the dispersion through said second screen to separate the large particle contaminants from the smaller particles that do pass through the second screen, and measuring the weight of the separated large particle contaminants that did not pass through the second screen.

2. The method of claim 1, wherein said carbon black sample weighs at least about 1000 grams.

3. The method of claim 1, wherein said carbon black sample weighs from about 1500 grams to about 2500 grams.

4. The method of claim 1, wherein said dispersing agent comprises at least one organic solvent in an aqueous solution.

5. The method of claim 1, wherein said dispersing agent comprises a glycol ether.

6. The method of claim 1, wherein said dispersing agent comprises 2-butoxyethanol.

7. The method of claim 1, wherein said dispersing agent comprises an alcohol amine.

8. The method of claim 1, wherein said dispersing agent comprises ethanolamine.

9. The method of claim 1, wherein said dispersing agent comprises an alcohol alkoxylate.

10. The method of claim 1, wherein said dispersing agent comprises nonyl phenyl ethoxylate.

11. The method of claim 1, wherein said dispersing agent comprises two or more compounds selected from a glycol ether, an alcoholamine, and an alcohol alkoxylate.

12. The method of claim 1, wherein said dispersing agent comprises a glycol ether, an alcoholamine, and an alcohol alkoxylate.

13. The method of claim 1, wherein said dispersing agent comprises 2-butoxyethanol and ethanolamine.

14. The method of claim 13, wherein said dispersing agent further comprises nonyl phenol ethoxylate.

15. The method of claim 1, further comprising dividing the measured weight of separated contaminants from the weight of said sample to determine the concentration of contaminants in said sample.

16. The method of claim 15, further comprising comparing the determined concentration to predetermined values for the same type of carbon black to predict the amount of macro defect formation in an extrudable composition.

17. The method of claim 16, wherein said extrudable composition comprises EPDM.

18. The method of claim 1, wherein said first-mentioned screening step comprises washing the carbon black sample with water at a pressure of from about 15 psi to about 35 psi.

19. The method of claim 1, wherein said first-mentioned screening step comprises washing the carbon black sample with water at a pressure of from about 22 psi to about 27 psi.

20. The method of claim 1, wherein said first-mentioned screening step comprises washing the carbon black sample with a stream of water having a flow rate of about 1.5 gallons per minute.

21. The method of claim 1, wherein screening the carbon black sample comprises passing the carbon black through about a 120 mesh sieve screen.

22. The method of claim 1, further comprising performing an image analysis of said separated large particle contaminants and using said image analysis to determine the particle size distribution and the number of particles per unit weight of the separated large particle contaminants.

23. The method of claim 1, further comprising performing an electron scanning microscopy on said separated large particle contaminants to determine the amount of soft coke in said separated large particle contaminants.

24. The method of claim 1, further comprising performing disc centrifuge photosedimentometry on said separated large particle contaminants to determine the amount of soft coke in said separated large particle contaminants.

25. A method of determining the amount of contaminants in a carbon black sample, comprising
screening a known amount of carbon black through a first screen to separate larger particles in the sample which do not pass through the first screen from smaller particles that do pass through the first screen,
applying a magnetic force to the separated larger particles to separate magnetic particles in the separated larger particles from non-magnetic particles in the separated larger particles, and
measuring the amount of separated magnetic particles.

26. The method of claim 25, wherein said carbon black sample weighs at least about 1000 grams.

27. The method of claim 25, wherein said carbon black sample weighs from about 1500 grams to about 2500 grams.

28. The method of claim 25, further comprising treating the non-magnetic components of the separated larger particles with a sufficient amount of a dispersing agent or a sufficient physical force to break down agglomerated carbon black particles in the non-magnetic components into smaller carbon black aggregates and form a treated mixture, and screening the treated mixture to separate larger particles in the mixture which do not pass through the screen from smaller particles in the mixture which do pass through the screen.

29. The method of claim 28, further comprising determining the concentration of contaminants in said sample by measuring the weight of said larger particles in the mixture which do not pass through the screen and dividing the sum of the measured weight of separated magnetic contaminants plus the measured weight of the larger particles in the mixture which do not pass through the screen, by the weight of said sample, to determine the concentration of contaminants.

30. The method of claim 29, further comprising comparing the determined concentration to predetermined values for the same type of carbon black to predict the amount of macro defect formation in an extrudable composition.

31. The method of claim 30, wherein said extrudable composition comprises EPDM.

32. The method of claim 25, wherein said screening comprises washing said carbon black sample with water at a pressure of from about 15 psi to about 35 psi.

33. The method of claim 25, wherein said screening comprises washing said carbon black sample with water at a pressure of from about 22 psi to about 27 psi.

34. The method of claim 28, wherein said larger particles in the mixture which do pass through the screen are treated by contact with water at a pressure of about 25±1 psi.

35. The method of claim 28, wherein said larger particles in the mixture which do pass through the screen are contacted with a dispersing agent which breaks down larger agglomerated carbon black particles in the larger particles in the mixture into smaller carbon black aggregates.

36. The method of claim 35, wherein said dispersing agent comprises an aqueous solution containing at least one organic solvent.

37. The method of claim 35, wherein said dispersing agent comprises two or more compounds selected from a glycol ether, an alcoholamine, and an alcohol alkoxylate.

38. The method of claim 35, wherein said dispersing agent comprises a glycol ether, an alcoholamine, and an alcohol alkoxylate.

39. The method of claim 25, wherein screening the carbon black sample comprises passing the carbon black sample through a screen having a mesh size of about 120 mesh.

40. The method of claim 25, further comprising performing an image analysis of said non-magnetic components of the separated larger particles and using said image analysis to determine the particle size distribution and the number of particles per unit weight of the non-magnetic components of the separated larger particles.

41. The method of claim 25, further comprising performing an electron scanning microscopy on said non-magnetic components of the separated larger particles to determine the amount of soft coke in said non-magnetic components of the separated larger particles.

42. The method of claim 25, further comprising performing disc centrifuge photosedimentometry on said separated non-magnetic components of the separated larger particles to determine the amount of soft coke in said non-magnetic components.

43. The method of claim 25, wherein after screening the carbon black sample, the separated larger particles are treated with a sufficient amount of a dispersing agent or a sufficient physical force to break down agglomerated carbon black particles and to form a treated mixture before applying the magnetic force to the separated larger particles.

44. The method of claim 43, wherein the treated mixture is screened through a second screen to separate larger particles in the mixture which do not pass through the screen from smaller particles in the mixture which do pass through the screen before applying the magnetic force to the separated larger particles.

* * * * *